United States Patent [19]
Burke et al.

[11] Patent Number: 5,929,300
[45] Date of Patent: Jul. 27, 1999

[54] POLLEN-BASED TRANSFORMATION SYSTEM USING SOLID MEDIA

[75] Inventors: John J. Burke; Melvin J. Oliver; Jeffrey P. Velten, all of Lubbock, Tex.

[73] Assignee: The United States of America as represented by the Secretary of Agriculture, Washington, D.C.

[21] Appl. No.: 08/892,735

[22] Filed: Jul. 15, 1997

[51] Int. Cl.$^6$ .............................. C12N 5/04; C12N 15/84; C12N 15/82; A01H 4/00
[52] U.S. Cl. .......................... 800/278; 435/414; 435/415; 435/419; 435/469; 800/294; 800/312; 800/314; 800/317.3; 800/260
[58] Field of Search .............................. 435/172.3, 252.2, 435/431, 410, 414, 415, 418, 419, 468, 469; 800/205, DIG. 26, DIG. 27, DIG. 43, 278, 294, 295, 298, 312, 314, 317.3, 260; 47/58

[56] References Cited

U.S. PATENT DOCUMENTS

| | | | |
|---|---|---|---|
| 4,743,548 | 5/1988 | Crossway et al. | 435/172.3 |
| 5,013,552 | 5/1991 | Samir Amer et al. | 424/408 |
| 5,066,594 | 11/1991 | DeBonte et al. | 435/240.4 |
| 5,100,792 | 3/1992 | Sanford et al. | 435/172.1 |
| 5,120,657 | 6/1992 | McCabe et al. | 435/287 |
| 5,177,010 | 1/1993 | Goldman et al. | 435/172.3 |
| 5,187,073 | 2/1993 | Goldman et al. | 435/172.3 |
| 5,569,597 | 10/1996 | Grimsley et al. | 435/172.3 |
| 5,629,183 | 5/1997 | Saunders et al. | 435/172.3 |

FOREIGN PATENT DOCUMENTS

| | | |
|---|---|---|
| 301316 | 2/1989 | European Pat. Off. . |
| 538698 | 12/1976 | U.S.S.R. . |
| 1708849 | 1/1992 | U.S.S.R. . |

OTHER PUBLICATIONS

Sussmuth et al, Agrobacterium–mediated transfer of the GUS gene into Pollen of Petunia, Botanica Acta, vol. 104, p. 72, 1991.

Stewart, J.McD., Chapter 20, Integrated Events in the Flower And Fruit, in Cotton Physiology, (Mauney & Stewart, eds.), pp. 270–271, 1986.

Potrykus, I., Gene Transfer into Plants: Assessment of Published Approaches and Results, Ann. Rev. Plant Physiol. Plant Mol. Biol., vol. 42, pp. 207–208, 218–219, 1991.

Landridge et al, Transformation of cereals via Agrobacterium and the pollen pathway: a critical assessment, Plant J., vol., 2, pp. 631–638, 1992.

Sangwan et al, Agrobacterium–mediated transformation of pollen embryos in *Datura innoxia* and *Nicotiana tabacum*: production of transgenic haploid and fertile homozygous dihaploid plants, Plant Sci., vol. 95, pp. 99–106, especially pp. 105–106, 1993.

Mulcahy, et al., The Effect of Supplemented Media on the Growth In Vitro of Bi–and Trinucleate Pollen, *Plant Science*, 55:213–216 (1988).

Huang et al. Transfer of resistance of disease–sensitive cotton by introduction of exogenous blighted cotton DNA. *Jiangsu Prefectural Academy of Agricultural Science/Chinese Academy of Science* 7 pages (original and translation).

Huang, Junqi et al., Exogenous Haidaomian DNA–Induced Variation of Zhongmian Character, *Chinese Academy of Science*, pp. 16–19 (original and translation).

Heslop–Harrison, et al. The Receptive Surface of the Angiosperm Stigma, *Ann. Bot.,* 41:1233–1258 (1977). and Plates 1–4.

Stewart, Ch. 20, Integrated events in the flower and fruit in *Cotton Physiology,* (Mauney & Stewart, eds.) The Cotton Foundation, pp. 261, 270–272, 731, 761.

Cheng, et al. Methods of maize pollen germination in vitro, collection, storage, and treatment with toxic chemicals; recovery of resistant mutants. *Maize Genet. Coop. Newsl.,* 50:11–13.

Ni, et al. Cultivation of transgenic insect–resistant cotton. *Chinese Academy of Agricultural Science.* 9 pages (original and translation).

Booy, et al. Attempted pollen–mediated transformation of maize. *J. Plant Physiol.,* 135:319–324 (1989).

Brewbaker, et al., Essential role of calcium ion in pollen germination and pollen tube growth. *Amer. J. Botany,* 50(9):859–865 (Oct. 1963).

Taylor. Germination of cotton (*Gossypium hirsutum* L.) pollen on an artificial medium. *Crop Science* 12:243–244 (Mar.–Apr. 1972).

Smith et al. Expression of GUS and CAT activities using electrotransformed pollen. *Plant Science,* 104:49–58 (1994).

(List continued on next page.)

*Primary Examiner*—David T. Fox
*Assistant Examiner*—Ashwin D. Mehta
*Attorney, Agent, or Firm*—Rothwell, Figg, Ernst & Kurz

[57] ABSTRACT

A medium is disclosed that supports pollen germination and pollen tube growth in the presence of Agrobacterium, the medium comprising agarose, sucrose, $NO_3$, $MnSO_4$, $H_3BO_3$, $MgSO_4$ and gibberellic acid. A method is disclosed for the genetic transformation of plants and lines by a pollen-based Agrobacterium-mediated transformation. The method comprises the steps of obtaining pollen from a first plant, applying a lawn of Agrobacteria to a solid pollen culture medium, the Agrobacterium comprising at least one heterologous gene sequence capable of being transferred to a plant cell, applying the pollen to the solid medium, allowing the pollen to germinate and grow on the medium, whereby the Agrobacterium attaches to the pollen tube or mediates transfer of the heterologous gene sequence to the germinating pollen to obtain transgenic pollen, applying the transgenic pollen to the stigma of a second plant capable of being fertilized by the pollen of the first plant, thereby fertilizing the second plant, obtaining transgenic seed from the second plant and germinating the transgenic seed to obtain a transgenic plant. The method is particularly suited for use with so-called "dry stigma" pollen.

7 Claims, 1 Drawing Sheet

OTHER PUBLICATIONS

Singh et al. Effect of temperature on in vitro pollen germination in pigeonpea. *Biologia Plantarum,* 34(5–6):461–464 (1992).

Shivanna et al. Polyethylene glycol improves the in vitro growth of Brassica pollen tubes without loss in germination. *J. Exper. Botany,* 46(292):1771–1774 (Nov. 1995).

Moreno et al. In–situ seed production after pollination with in–vitro–matured, isolated pollen. *Planta,* 176:145–148 (1988).

Gawel et al. Effect of pollen–style interaction on the pollen tube growth of *Gossypium hirsutum. Theor. Appl. Genet.,* 72:84–87 (1986).

Alexander et al. An improved cellophane method for in vitro germination of recalcitrant pollen. *Stain Technology,* 64(5):225–227 (1989).

POLLEN-BASED TRANSFORMATION SYSTEM USING SOLID MEDIA

TECHNICAL FIELD

The present invention relates to the general field of genetic engineering of plants, in particular to the transformation of exogenous genetic material into the germ line of plant lines by a pollen-based Agrobacterium transformation.

BACKGROUND OF THE INVENTION

Transformation of cultured plant cells using recombinant Agrobacterium, followed by regeneration of the transformed cells into whole plants, has become the standard means for producing transgenic plants. Various methods employing Agrobacterium vectors have been developed and are known in the art, including the binary plasmid system disclosed in U.S. Pat. No. 4,940,838 (Schilperoort, et al., Jul. 10, 1990), and the so-called co-integrate plasmid system disclosed in U.S. Pat. No. 4,693,976 (Schilperoort, et al., Sep. 15, 1987). Most current methods employ disarmed Agrobacterium, that is, Agrobacterium that has had the tumor-inducing functions deleted or inactivated, so that transformation does not cause tumorous growth, but rather permits growth of normal tissue callus capable of being regenerated into a normal plant.

The use of Agrobacterium, as with most other transformation techniques, has a drawback. In order to obtain a plant that is uniformly transformed (that is, has the heterologous DNA present in every cell) it is necessary to transform individual cells and regenerate therefrom a somatic clone. The cells of some plant species are not easily maintained in tissue culture, and are not easily regenerated into somatic clones. One technique that has been investigated to overcome these obstacles is the use of pollen as a vector. By transforming pollen, then using the transgenic pollen to fertilize a receptive plant, transgenic seed containing the heterologous DNA can be produced. The transgenic seed can be germinated to naturally produce a transgenic plant.

The terms "transgenic pollen" or "transformed pollen" as used in connection with the present invention are defined as Agrobacterium-treated pollen or germinated pollen that is capable of delivering DNA, whether within the pollen or germinated pollen or within an Agrobacterium that is associated with the pollen tube, to the ovum. While not wishing to be bound by theory, there are at least two possible mechanisms by which the treated germinated pollen (i.e. "transgenic pollen" or "transformed pollen" as the term is used hereinafter) of the present invention could be delivering the heterologous DNA to the plant ovum. One possible mechanism involves the introduction of the heterologous DNA into the pollen germ cell itself, the heterologous DNA then being carried down the pollen tube to the ovum along with endogenous DNA during fertilization. Another possible mechanism involves adhesion of Agrobacterium to the elongating pollen tube, whereby the bacterium is carried to the ovum by the tube, where transformation of the ovum or developing zygote occurs. The existence of several possible mechanisms necessitates the precise definition of the terms "transgenic pollen" and "transformed pollen" as set forth above.

The use of pollen as a vector is not without its problems, however. In order to effectively and efficiently obtain transgenic pollen it is necessary first to germinate the pollen grain. In an Agrobacterium based system this is required in order to allow for either transfer of the heterologous DNA from the bacteria to the pollen germ cell or for effective attachment of the bacterium of the growing pollen tube. Because of the time factor this necessitates an in vitro system for pollen germination and pollen tube growth. The cultivation of germinating pollen and pollen tubes in vitro has proved difficult, as the grains tend to rupture in the culture medium, resulting in the release and degradation of their DNA. Pollen survival has been low, and subsequent plant transformation efficiency poor. Some pollen types, so-called "dry" or "dry stigma" pollens (such as cotton pollen) are so sensitive to moisture that efforts to obtain pollen germination and sustained pollen tube growth have failed. Thus, it has proved difficult to culture and obtain transformed pollen effectively in vitro for use as a vector for producing transgenic plants. U.S. Pat. No. 5,066,594 (DeBonte et al., Nov. 19, 1991) contains a review of in vitro pollen germination methods and pollen-based methods of plant transformation, and difficulties encountered in their use. DeBonte et al. state that the consensus in the art is that calcium, boron and an osmoticum (usually sucrose) are critical components of a germination medium in order to obtain pollen germination. Col. 2, lines 10–22. DeBonte also notes that lysis of the pollen wall has been found to occur in pollen germination medium that does not contain agar. Col. 2, lines 44–49. A medium containing calcium, boron, lysine, glutamic acid and sucrose was found to give fair germination rates with pollen that had been stored for 12 hours after anthesis, but the pollen grains demonstrated poor stability and tended to burst over time on the germination medium. Col. 2, lines 50–63.

It should be noted that DeBonte was discussing exclusively germination of wet stigma pollen, and the use of liquid or semi-liquid germination media.

DeBonte proposed an aqueous "stabilization solution," to be used in conjunction with an aqueous germination medium, to permit maintenance of germinating pollen in culture for a time sufficient to allow transformation by Agrobacterium. Once germinated, the pollen would be transferred to the stabilization solution and incubated with the Agrobacterium vector to effect transformation of the pollen. DeBonte did not demonstrate that this method actually worked for transforming pollen, nor that the pollen was capable of fertilizing a receptive plant after being thus treated.

Other methods proposed for transforming pollen include microparticle bombardment (U.S. Pat. No. 5,100,792; U.S. Pat. No. 5,120,657), microinjection (U.S. Pat. No. 4,743,548) and electroporation (U.S. Pat. No. 5,629,183). The first requires elaborate and expensive equipment, while the second requires delicate manipulation of individual pollen grains. Neither method has been shown to be effective in producing viable transgenic pollen capable of fertilizing a receptive plant. The third, although effective, again requires elaborate and expensive equipment, highly knowledgeable and trained personnel and the pollen has to be exposed to aqueous conditions; a lethal environment for dry stigma pollen under normal circumstances.

A need remains for a simple, effective means of germinating and obtaining transgenic pollen in vitro, particularly dry stigma pollen, that is efficient and permits easy fertilization of receptive plants with the transgenic pollen.

SUMMARY OF THE INVENTION

The present invention relates to a method for genetically transforming plants comprising the steps of: producing a medium capable of inducing and supporting pollen tube growth in vitro and with the addition of Agrobacteria also enhances pollen tube growth; placing a lawn of transgenic Agrobacteria that enhance pollen tube growth on the surface of the germination medium; placing pollen on the germination medium; incubating the pollen and Agrobacteria in a controlled temperature and humidity environment to permit germination of the pollen, with subsequent production of transgenic pollen; transferring the transgenic pollen to the stigma of a receptive plant, preferably an emasculated plant, to effect fertilization of the receptive plant; harvesting transgenic seed from the fertilized plant; screening of seedlings from germinated transgenic seed with any standard selection agent system to confirm that transformation has occurred; further growth of seedlings to produce a mature fertile transgenic plant. The methods of the present invention provides superior pollen germination and plant transformation as compared to prior art methods, and are simple and economical. The invention has applicability to the germination of dry stigma pollens and production of transgenic dry stigma pollens. The present invention also has the advantage of not requiring in vitro cultivation of plant tissues, and not requiring regeneration of somatic clones from cultured plant cells.

DETAILED DESCRIPTION OF THE INVENTION

Figure 1:
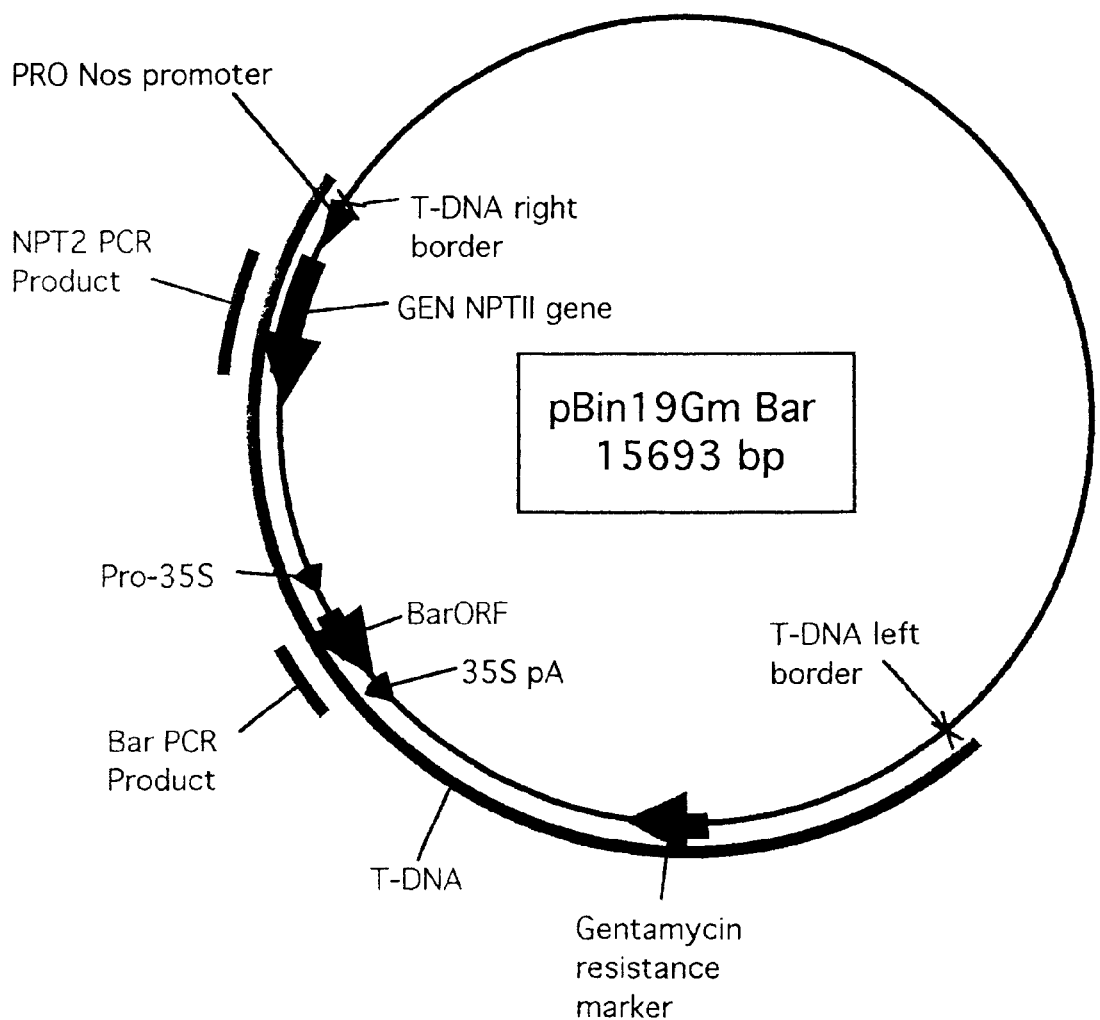
FIG. 1 depicts the plasmid pBin19GmBar used as a test plasmid for the present invention.

The present invention relates to an efficient method of producing transgenic plants using a pollen based Agrobacterium transformation system. In contrast to earlier attempts at using pollen as a transformation vector, the present invention provides a way to germinate and maintain pollen, especially dry stigma pollen, in vitro on a solid growth medium without lysis of the pollen, so that upon co-cultivation with Agrobacterium transgenic pollen can be efficiently produced. Transgenic pollen provides an efficient means of transforming plant germ lines without the necessity of using plant cell cultures and somatic regeneration of whole plants. The present method thus provides a means of transforming a variety of plants that are not otherwise easily transformed, or for which efficient means of somatic regeneration are not presently known or possible.

The germination media used with the present invention are solid media comprising agarose, sucrose, $KNO_3$, $MnSO_4$, $H_3BO_3$, $MgSO_4$ and gibberellic acid. Although pollen germination was supported by substitutions of maltose or glucose as the osmoticum, sustained cotton pollen tube growth required the presence of sucrose from among the sugars tested. The percent germination was also enhanced in media containing sucrose over that observed with maltose, glucose or fructose. A preferred medium comprises 10% agarose, 25% sucrose, 0.52 mM $KNO_3$, 3.06 mM $MnSO_4$, 1.66 mM $H_3BO_3$, 0.42 mM $MgSO_4.7H_2O$ and 1.0 $\mu M$ $A_3$ gibberellic acid. The pH of the medium should be in the range of 6.0 to 8.0 preferably about 7.6. The media is preferably poured into petri dishes immediately after autoclaving, covered, and stored in a refrigerator until needed.

These media will support the germination and growth of pollen from a variety of plants, and although it was designed especially for dry stigma plants (e.g., cotton)., it will also support the germination and pollen tube growth of wet stigma plants (tobacco and soybean). The media was also developed to act in a synergistic manner with Agrobacterium to enhance pollen tube growth, the exact mechanism of which has not been determined.

Transgenic pollen can be produced using any Agrobacterium-based vector system, including the binary vector system of U.S. Pat. No. 4,940,838 and the co-integrate vector system of U.S. Pat. No. 4,693,976.

The use of disarmed (non-tumorigenic) Agrobacterium is preferred. A preferred vector system is the binary system of U.S. Pat. No. 4,940,838. The selection of an appropriate vector system and transformation method from among the numerous ones disclosed in the prior art, and its use in the present invention, is well within the skill in the art. Likewise, methods for the growth and maintenance of Agrobacteria in vitro are well-known in the art, and the worker of ordinary skill will have no trouble finding suitable methods in the available literature.

The choice of the heterologous gene sequence to be introduced via the pollen, and ultimately into the plant, imposes no particular restrictions of the use of the present invention, the selection of the gene being governed by the characteristic that is desired to be imparted to the transgenic plant. Examples of the kinds of genes that can be used with the present invention include genes that impart herbicide resistance, insect resistance, disease resistance, modified starch production, modified protein production, modified fatty acid production, modified production of amino acids, altered flower color, altered flowering time, drought resistance, antisense genes that suppress endogenous gene function, or genes encoding a product that is isolated from the plant in purified form, such as a drug or antibody. Any gene construct expressible in a plant, capable of introduction into an Agrobacterium and transferable from the Agrobacterium into a plant cell may be used with the present invention. A preferred construct includes one or more selectable markers that enable selection of transformants, be they Agrobacterium or plant, and a plant-active promoter linked to the coding sequence. Such constructs are abundantly known in the art. The manner of assembling such constructs and introducing them into the Agrobacterium does not form a part of the present invention, and is well within the skill in the art.

Examples of plant chimeric genes and Agrobacterium vector construction are found in U.S. Pat. Nos. 5,352,605, 5,149,645, 5,034,322, 5,068,193 and 4,762,785.

Pollen for use in the present invention is collected from anthers, preferably from newly-dehiscent anthers, by shaking the flower over foil or by any other means that does not damage the pollen grains. Pollen is preferably collected just prior to use. Once collected, the pollen is placed on the surface of the solid germination media and allowed to germinate. Preferably, a lawn of Agrobacterium transformed with the desired heterologous gene sequence is applied to the surface of the media prior to the application of the pollen, most preferably immediately prior to application of the pollen. The presence of Agrobacterium has been found to give improved pollen germination and growth. The pollen is preferably spread uniformly over the surface of the medium in a thin layer, such as by gently shaking the plate and pouring off the excess pollen. Germination of the pollen is preferably carried out in a controlled temperature and humidity environment, with the temperature between about 20 and 32° C., most preferably between about 24 and 28° C., and humidity levels preferably between about 5% and 100%, most preferably at 80%. A convenient means for controlling humidity to the 80% level is to place the media plates above a layer of saturated ammonium sulfate for germination. Germination and pollen tube growth normally occurs within about 3–4 hours, with little or no lysis of pollen grains and pollen tubes. A preferred embodiment is the use of this invention with dry stigma pollen, most preferably with cotton pollen. Once the pollen tubes have germinated and been incubated with Agrobacterium for a time sufficient to allow for attachment of the bacteria or DNA transfer (normally 3–4 hours), the treated pollen can be used to pollinate a receptive plant (a plant of the same species, or a species capable of hybridizing with the pollen donor plant).

This may be accomplished by simply contacting the surface of the germination plate to the stigma of the receptive flower. In a preferred embodiment, the receptive flower is male-sterile or emasculated. The use of male-sterile or emasculated flowers prevents self-pollination and reduces the likelihood of pollination with non-transformed pollen from other plants. A preferred method for emasculating cotton flowers is to fill newly-opened flowers with water such that the anthers and stigma are saturated. By allowing the anthers and stigma to remain saturated with water for a period of time, preferably between 30 seconds and 30 minutes, pollen present in the flower, even germinating pollen, ruptures and is destroyed. Once pollen destruction is complete, the water is drained from the flower and the flower is ready for pollination. The stigma of the emasculated flower is preferably capped by some means until ready for pollination, to prevent accidental cross-pollination. It is most preferred to carry out this procedure prior to mid-afternoon (about 2:30), as flowers emasculated before this time show no significant reduction in seed set. Emasculation of cotton flowers has been shown to be between 95% and 100% effective using this technique.

Once the receptive plant is pollinated with the treated pollen, steps are preferably taken to prevent further accidental cross-pollination of the flower. This can include isolating the plant (such as in a greenhouse), capping the stigma or covering the entire flower to prevent entry of insect or wind-born, non-transgenic pollen. The pollinated plant can be allowed to grow normally and set seed. The seed thus produced can be termed putative transgenic seed, as it will be comprised of individual seeds within the total population that contain in their genome the heterologous DNA introduced into the pollen. The putative transgenic seed will germinate and grow into putative transgenic plants. The present invention can thus be seen to allow the production of putative transgenic plants without the need to use plant tissue culture and somatic clone regeneration. The population of putative transgenic plants can be screened as seeds, germinating seeds, seedlings or as mature plants to isolate true transgenic individual plants using any standard selectable and or screenable marker, such as kanamycin resistance or an indicator protein (e.g., aequorin or luciferin), or by the use of an herbicide, an herbicide resistance gene being used as the selectable marker in the gene construct introduced via the Agrobacterium-treated pollen. The screening for transgenic plants automatically selects for stable transformants (plants having the heterologous DNA stably integrated into their chromosomes), as only stably-transformed plants will have preserved the introduced sequences such that they would survive the screen.

DETAILED DESCRIPTION OF THE FIGURE

FIG. 1 represents the plasmid pBin19GmBar used as a test plasmid for the present method. The plasmid was constructed by inserting a chimeric 35S-bar gene into the plasmid pBin19 (Bevan, A Binary Plant Vector Strategy based on separation of Vir- and T-region of the *Agrobacterium tumefaciens* Ti-plasmid" *Nature,* 303:179–180 (1983); ATTC 37327). The plasmid contains in sequence a T-DNA right border sequence, a NOS promoter linked to the NPTII coding sequence, followed by a NOS terminator sequence, a CaMV 35S promoter linked to the Bar coding sequence, followed by a 35S polyadenylation sequence, and finally a gentamyacin gene inserted in the antisense direction as a selectable marker, followed by a T-DNA left border sequence.

EXAMPLE 1

Pollen Germination Medium

A solid medium to support pollen germination was prepared containing 10% agarose, 25% sucrose, 0.52 mM $KNO_3$, 3.06 mM $MnSO_4$, 1.66 mM $H_3BO_3$, 0.42 mM $MgSO_4.7H20$ and 1.0 μM $A_3$ gibberellic acid. The final pH was adjusted to 7.6. Immediately after autoclaving, the medium was poured into 35 mm×10 mm petri dishes, sealed with parafilm, and stored in a refrigerator until use.

EXAMPLE 2

Transgenic *Agrobacterium tumefaciens*

*Agrobacterium tumefaciens* strain EHA 101 was transformed with a "tester plasmid" pBin19Gmbar (pBin 19 containing a bacterial gentamycin resistance marker)that contains a chimeric 35S-bar gene. This plasmid is shown in FIG. 1. The chimeric 35S-bar gene was constructed by the insertion of the bar coding region (encoding the enzyme phosphinothricin acetyltransferase) from pAHC25 (Christensen et al 1992) into the multicloning site of pRTL2 (Gupta et al 1993) immediately downstream of a dual 35S promoter and upstream of the 35S terminator sequence to give pRTL2bar. The chimeric 35S-bar gene was isolated from pRTL2bar as a HindIII fragment and cloned into the multicloning site of the pBin 19Gm to give the final tester plasmid, pBIN 19Gmbar. The constructed pBIN 19Gmbar was introduced into the *A. tumefaciens* line EHA 101 by a standard electroporation method (Walkerpeach and Velten, 1994). Transformants were selected by growth on LB agar (Miller, 1973) plates containing 25 μg/ml gentamycin. The presence of the pBIN 19Gmbar plasmid was further confirmed by PCR. The transformed Agrobacterium were then grown in 1 ml of LB broth, containing 25 μg/ml gentamycin and 50 μM acetosyringone for 18 hours at 28° C. Following the 18 hour incubation, 200 μl of the bacteria culture were transferred to L-broth plates containing acetosyringone and gentamycin. The inoculated L-broth plates were incubated at 28° C. overnight.

Twenty-four hours later, pollen germination plates of Example 1 were inoculated with a lawn of transformed Agrobacterium by first pressing a 50 ml beaker covered with a sterile piece of velvet onto the surface of the inoculated L-broth plates, then pressing the velvet to the surface of a pollen germination plate.

EXAMPLE 3

Germination and Production of Transgenic Pollen

Pollen was obtained from newly opened cotton flowers by shaking onto a piece of foil. The pollen thus obtained was placed onto one of the inoculated pollen germination plates of Example 2 and the plate gently shaken to completely cover the surface of the medium with pollen. Excess pollen was transferred to a second pollen germination plate and the process repeated until several germination plates covered with pollen were obtained. The germination plates were then placed without covers above a layer of saturated ammonium sulfate giving a humidity level of approximately 80% in a sealed humidity chamber and incubated at 28° C. for 30 min and then 24° C. for 3–4 hours to allow germination and production of transgenic pollen. Pollen thus treated had a germination rate of >75%. Little or no pollen tube lysis was observed. Humidity levels of 100% resulted in pollen tube lysis, and humidity levels below 60% reduced pollen germination.

The process has been repeated with pollen from tobacco and soybeans with essentially the same pollen survival rates, germination frequency and tube growth kinetics.

EXAMPLE 4

Pollination and Production of Transgenic Plants

Cotton flowers were emasculated by filling the flower with enough water to cover the stigma and anthers. After 30 seconds, the water was removed and the stigmas were capped with a plastic bulb to prevent fertilization until desired. This procedure was found to be 95%–100% effective in emasculating the cotton flower by causing the rupture of pollen, and germinating pollen tubes, thereby preventing self-fertilization. Flowers thus emasculated were pollinated with the germinating, treated pollen of Example 3 by simply uncapping the stigma, drying the stigma surface with a Kimwipe and contacting the dry stigma with the surface of the pollen germination plates.

The pollinated plants were grown in greenhouses under hydroponic conditions in rockwool pads and allowed to set seed. The seed obtained from these plants were ginned, delinted and hot water treated to enhance germination. The seeds were planted in 2 gallon pots containing Sunshine #3, special fine potting mix (Sun Gro Horticultre, Inc., Canada), grown for 2 weeks (primary leaf is evident) prior to the seedling screening. Seedlings were screened for transformants by spraying with ½ to ¾ the recommended dosage of Liberty (glufosinate) herbicide. This method was found to be 100% effective for identifying transgenic plants that express the introduced chimeric gene and indicated that the rate of transformation was approximately 1 transformant for every 3,000 seeds analyzed.

REFERENCES

Christensen, A. H., Sharrock, R. A., and Quail, P. H. 1992. Maize polyubiquitin genes: structure, thermal perturbation of expression and transcript splicing and promoter activity following transfer to protoplasts by electroporation. Plant Mol Biol 18:675–689

Miller, J. 1973. Experiments in molecular biology. Cold Spring Harbor Laboratory, New York.

Gupta, A. S., Heinen, J. L., Holaday, A. S., Burke, J. J. and Allen, R. D. 1993. Increased resistance to oxidative stress in transgenic plants that overexpress chloroplastic Cu/Zn superoxide dismutase. Proc. Natl. Acad. Sci. 90:1629–1633.

Walkerpeach, C. and J. Velten (1994). Agrobacterium-mediated gene transfer to plant cells: cointegrate and binary vector systems. In "Plant Molecular Biology Manual". Eds. S. B. Gelvin, R. A. Shilperoort, D. P. S. Verma. Published by Kluwer Academic Publishers., Dordrecht, The Netherlands, Sec.B1: 1–19.

We claim:

1. A method for producing a transgenic plant comprising:
    a. obtaining pollen from a first plant,
    b. applying a lawn of Agrobacteria to a solid pollen culture medium, the Agrobacteria comprising at least one heterologous gene sequence capable of being transferred to a plant cell,
    c. applying the pollen to the solid medium,
    d. allowing the pollen to germinate and grow on the medium, thereby producing transgenic pollen,
    e. applying the transgenic pollen to the stigma of a second plant capable of being fertilized by the pollen of the first plant, thereby fertilizing the second plant,
    f. obtaining transgenic seed from the second plant,
    g. germinating the transgenic seed to obtain a transgenic plant.

2. The method of claim 1, wherein the first and second plants are selected from the group consisting of tobacco plants, cotton plants and soybean plants.

3. The method of claim 1, wherein the solid pollen culture medium comprises 10% agarose, 25% sucrose, 0.52 mM $KNO_3$, 3.06 mM $MnSO_4$, 1.66 mM $H_3BO_3$, 0.42 mM $MgSO_4.7H_2O$ and 1.0 $\mu M$ $A_3$ gibberellic acid.

4. The method of claim 1, wherein the plants are dry stigma pollen plants.

5. The method of claim 4, when the plants are cotton plants.

6. The method of claim 5, wherein the second cotton plant is an emasculated cotton plant.

7. The method of claim 1, comprising the additional step of emasculating the second plant prior to the application of the transgenic pollen thereto.

* * * * *